(12) United States Patent
Linenkugel et al.

(10) Patent No.: US 8,529,435 B2
(45) Date of Patent: Sep. 10, 2013

(54) MAGNETIC SCOPE MANIPULATOR

(75) Inventors: Duane Linenkugel, Cincinnati, OH (US); Robert M. Trusty, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1134 days.

(21) Appl. No.: 12/239,150

(22) Filed: Sep. 26, 2008

(65) Prior Publication Data
US 2010/0081876 A1 Apr. 1, 2010

(51) Int. Cl.
*A61B 1/04* (2006.01)
*A61B 1/00* (2006.01)

(52) U.S. Cl.
USPC ............ 600/114; 600/104; 600/127; 600/129

(58) Field of Classification Search
USPC .......................................... 600/114, 127, 129
See application file for complete search history.

(56) References Cited

U.S. PATENT DOCUMENTS

| | | | | |
|---|---|---|---|---|
| 5,681,260 | A * | 10/1997 | Ueda et al. | 600/114 |
| 5,813,976 | A | 9/1998 | Filipi et al. | |
| 6,033,413 | A * | 3/2000 | Mikus et al. | 606/108 |
| 6,059,719 | A * | 5/2000 | Yamamoto et al. | 600/127 |
| 6,293,909 | B1 * | 9/2001 | Chu et al. | 600/121 |
| 7,169,104 | B2 * | 1/2007 | Ueda et al. | 600/104 |
| 7,988,618 | B2 * | 8/2011 | Mikkaichi et al. | 600/114 |
| 2004/0158138 | A1* | 8/2004 | Kilcoyne et al. | 600/350 |
| 2005/0165272 | A1* | 7/2005 | Okada et al. | 600/114 |
| 2007/0157937 | A1 | 7/2007 | Mikkaichi et al. | |
| 2007/0161855 | A1 | 7/2007 | Mikkaichi et al. | |
| 2008/0045803 | A1 | 2/2008 | Williams et al. | |

FOREIGN PATENT DOCUMENTS

| | | |
|---|---|---|
| EP | 1808134 A2 | 7/2007 |
| JP | 08256973 A | 10/1996 |

OTHER PUBLICATIONS

International Preliminary Report on Patentability, PCT Application No. PCT/US2009/057748, dated Mar. 29, 2011.
International Search Report, PCT Application No. PCT/US2009/057748, dated Feb. 2, 2010.

* cited by examiner

*Primary Examiner* — Alireza Nia
(74) *Attorney, Agent, or Firm* — Nutter McClennen & Fish LLP

(57) ABSTRACT

Devices and methods are provided for manipulating scoping devices, surgical tools, and/or tissue. An exemplary system for manipulating a scoping device can include a scoping device having a working channel, a tether extending through the working channel, and an internal coupling member attached to the tether and positioned adjacent to a distal end of the scoping device. The internal coupling member can be magnetically coupled to an external coupling member. An exemplary method for manipulating a scoping device can include inserting at least a portion of a scoping device into a body cavity and positioning an external coupling member proximate to an external surface of tissue such that the external coupling member magnetically couples through the tissue to an internal coupling member disposed within the body cavity and attached to a tether passed through at least one working channel of the scoping device.

12 Claims, 12 Drawing Sheets

MAGNETIC SCOPE MANIPULATOR

The present invention relates to methods and devices for performing surgical procedures, and in particular to methods and devices for manipulating surgical tools and/or tissue.

BACKGROUND OF THE INVENTION

In many surgical procedures, a scoping device is used to view, engage, and/or treat tissue in a number of ways to achieve a diagnostic or therapeutic effect. In endoscopic procedures, the scoping device is inserted through a natural orifice, such as the mouth, anus, vagina, or urethra, and is advanced along a natural lumen or other pathway to position a distal end of the device at a surgical site. In laparoscopic procedures, one or more small incisions are formed in the patient and a trocar or other device is inserted through the incision to provide a working channel into a body cavity, through which the scoping device can be passed.

Endoscopic procedures often require the use of a flexible shaft to accommodate a tortuous pathway through a body lumen or other pathway to the surgical site. The flexibility of such scoping devices makes them very useful for diagnosing, evaluating, or operating within body lumens. Once the scope exits the constraints of a lumen however, the flexible nature of the scope makes maneuvering difficult. The scope tip can be actively articulated as it is advanced in the patient's body, however the flexible portion of the scope proximal to the articulating tip can passively bend or buckle unpredictably.

For example, in many procedures performed within the peritoneal cavity, the patient is placed in a supine position and the peritoneal cavity is insufflated. Gravity causes the organs within the cavity to lie on the cavity's dorsal wall. A surgeon attempting to access a surgical site within the cavity with a scoping device using either a transvaginal or transrectal approach must push the scoping device through these organs, along the dorsal wall of the cavity. Successfully pushing a flexible scoping device through such obstacles can be incredibly difficult and time-consuming, as the tendency is for the scope to simply coil up, rather than to push through the organs.

In addition, it is often desirable in endoscopic and other minimally invasive surgical procedures to have a leverage point within the patient for manipulating surgical tools, implants, or tissue. A flexible scoping device, by itself, does not provide adequate leverage at its distal end for performing such manipulations.

Accordingly, there is a need for improved methods and devices for efficiently guiding scoping devices to a surgical site and for manipulating objects or tissue within a patient.

SUMMARY OF THE INVENTION

The systems and methods disclosed herein can be useful to manipulate scoping devices and other objects or tissue within a patient. In one exemplary embodiment, a system for manipulating a scoping device is provided. The system can include a scoping device that has one or more working channels. In certain embodiments, the scoping device can be an endoscope. The system can also include a tether that extends through one of the working channels of the scoping device and that is attached at its distal end to an internal coupling member. The internal coupling member can be configured to be magnetically coupled to an external coupling member positioned external to the patient's body. The internal coupling member can include a feature formed thereon that is configured to be grasped by a tether or other surgical tool.

In an exemplary embodiment, the internal coupling member, the external coupling member, or both can include a magnet. For example, the internal coupling member can include one or more permant magnets, one or more non-permanent magnets, one or more electromagnets, or any combination thereof. Similarly, the external coupling member can include one or more permanent magnets, one or more non-permanent magnets, one or more electromagnets, or any combination thereof.

In another embodiment, the internal coupling member can have at least one working channel that is coaxial with the at least one working channel of the scoping device. In an exemplary embodiment, the internal coupling member can have a generally tubular shape and it can be removably attached to the distal end of the scoping device.

In other exemplary embodiments, the scoping device can include at least one magnetically-attracted collar disposed therearound. The collar can be slidably disposed around the scoping device and can have various configurations, such as a flexible mesh sleeve. The collar, like the internal and external coupling members, can include one or more electromagnets, one or more permanent magnets, one or more non-permanent magnets, or any combination thereof.

In another embodiment, a method is provided for positioning a scoping device at a desired location within a body cavity. The method can include inserting at least a portion of a scoping device into a body cavity, and positioning an external coupling member proximate to an external surface of tissue such that the external coupling member magnetically couples through the tissue to an internal coupling member. The internal coupling member can be disposed within the body cavity and can be attached to a tether passed through at least one working channel of the scoping device. In certain embodiments, the external coupling member can magnetically hold the internal coupling member against an interior surface of the tissue.

In another embodiment, the method can include manipulating the external coupling member and the scoping device to position the scoping device at a desired viewing angle with respect to at least one anatomical structure within the body cavity. In still other embodiments, the method can include manipulating the external coupling member to position the internal coupling member at a desired location. The method can also include advancing the scoping device along the tether and/or magnetically coupling at least one collar disposed around the scoping device at a location proximal to a distal end to the internal coupling member. The method can also include magnetically coupling at least one collar disposed around the scoping device through the tissue to the external coupling member.

In still further embodiments, a method for altering the position of an anatomical structure is provided. The method can include attaching a suture anchor to an anatomical structure, attaching a tether extending from an internal coupling member to the suture anchor, and positioning an external coupling member on an external tissue surface to magnetically engage the internal coupling member through tissue and thereby alter a position of the anatomical structure. In certain embodiments, the method can include delivering the internal coupling member and the tether into a body cavity using a scoping device prior to attaching the tether to the suture anchor.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In general, various devices and methods are provided for manipulating a scoping device, tissue, and/or other objects within a subject. In one exemplary embodiment, an internal coupling member is provided for coupling to a distal end of an insertion instrument, such as a scoping device. The internal coupling member can include a tether coupled thereto for guiding the scoping device therealong to position the scoping device in a desired position, and/or for coupling to tissue to manipulate or otherwise position tissue as desired. In an exemplary embodiment, the internal coupling member can be magnetic to allow an external coupling member, which can also be magnetic, to magnetically engage the internal coupling member through tissue. With the internal coupling member held against an internal tissue surface, the tether extending from the internal coupling member can be used to guide a scoping device or other device therealong, or can attach to tissue to maintain the tissue in a desired orientation. The tether can also be used for various other purposes as may be needed depending on the procedure being performed.

Figure 1A:
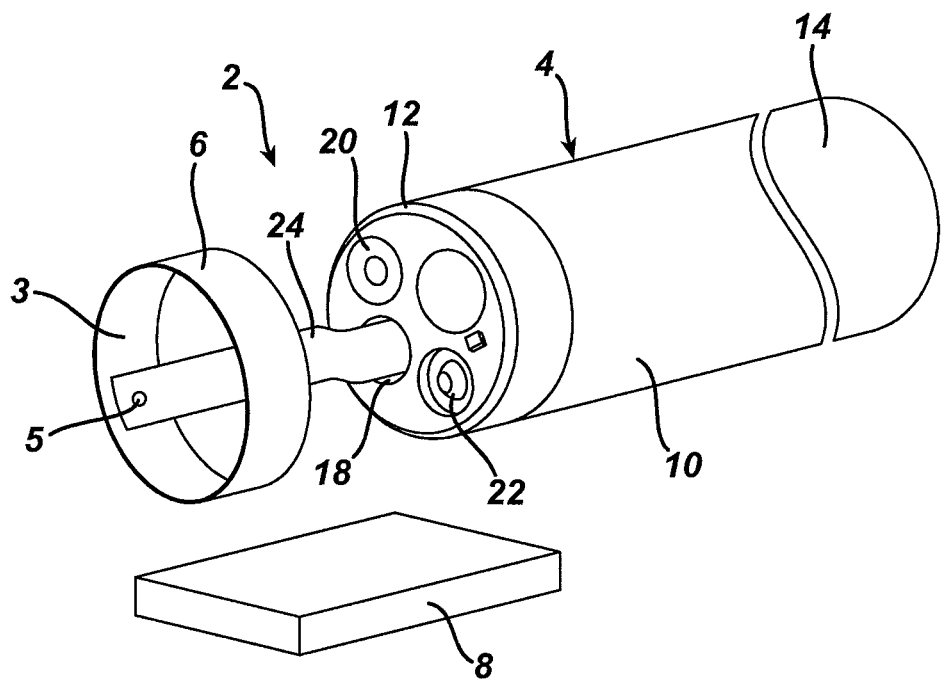
FIG. 1A is a perspective view of an external coupling member and an internal coupling member configured to be front-loaded into a scoping device.

FIG. 1A illustrates one exemplary embodiment of a magnetic scope manipulating system 2. As shown, the system includes a scoping device 4, an internal coupling member 6, and an external coupling member 8. The scoping device 4 is generally in the form of an elongate cylindrical body 10 having a distal end 12 and a proximal end 14. A handle 16 (shown in FIG. 2D) or other mechanism can be provided at the proximal end 14 of the scoping device 4 to facilitate grasping of the scoping device 4 by a surgeon. As is well known in the art, the distal portion of the scoping device can include an articulating section to permit a surgeon to control certain movements of the distal tip of the scoping device 4. The scoping device 4 can also include one or more working channels 18, a light delivery channel 20, and/or a viewing channel 22. The working channel 18 can permit various surgical tools and devices to be passed from outside of the patient to the internal surgical site. The light delivery channel 20 can comprise one or more optical fibers that can illuminate an area adjacent to the distal end 12 of the scoping device 4 by directing light from a light source positioned outside of the patient through the scoping device 4. Alternatively, the light source can be positioned within the light delivery channel 20 and can be positioned either near or at the distal end of the scoping device 4. The light source can optionally include an electronic illuminating element, such as a LASER or LED. The viewing channel 22 can comprise one more lenses through which the area adjacent to the distal end 12 of the scoping device 4 can be viewed from outside of the patient. The proximal end of the viewing channel 22 can be coupled to a monitor for displaying the view being transmitted through the viewing channel 22. A person skilled in the art will appreciate that virtually any scoping device (e.g., gastroscope, colonoscope, cystoscope, or laparoscope) known in the art can be used, or that various other insertion instruments having one or more lumens extending therethrough can be used with the devices and methods disclosed herein.

As indicated above, the internal coupling member 6 can be configured to couple to a distal end or distal portion of the scoping device 4 (or other insertion instrument) such that the internal coupling member 6 can be delivered into a body cavity by the scoping device 4. The internal coupling member 6 can then be released from the scoping device 4 to allow the internal coupling member 6 to be magnetically engaged through tissue by an external coupling member 8. The tether 24 extending from the internal coupling member 6 can be used as a guide for positioning the scoping device 4, and/or for attaching to tissue for positioning the tissue, or for various other uses.

The internal coupling member can have various shapes and/or configurations. In one embodiment, the internal coupling member is in the form of a generally cylindrical body. The internal coupling member can have virtually any shape however, including for example cubic, conical, spherical, tubular, etc. In embodiments where the internal coupling member is positioned adjacent to or near the distal end of the scoping device, it can be desirable for the internal coupling member to include one or more channels that are coaxial with the various channels in the scoping device, so that the internal coupling member does not obstruct the view through the scoping device and so that tools or other objects passed through the scoping device can in turn be passed through the internal coupling member. In the illustrated embodiment, a tubular shape is used to permit visualization and passage of objects through the internal coupling member 6. In one embodiment, the internal coupling member 6 can include a stalk or other feature protruding from its surface to facilitate grasping with various surgical tools.

The internal coupling member can have virtually any size. In an exemplary embodiment, the internal coupling member can have a diameter that is less than or equal to the diameter of the distal end of the scoping device, so that it can act like an extension of the scoping device. The size, mass, and composition of the internal coupling member 6 can be selected based on the relative magnetic strength of the external coupling member 8, the body cavity in which the scoping device is operating, the thickness of a patient's tissue, and/or based on other factors related to the operation being performed. In one embodiment, the internal coupling member includes a disk-shaped permanent magnet with a stalk protruding from its surface and has a diameter of approximately 12 mm, a thickness of approximately 6 mm, a stalk elevation of approximately 10 mm, and a mass of approximately 9 g.

Since the internal coupling member 6 is used to magnetically couple to an external coupling member 8, the internal coupling member 6 preferably includes at least one magnet. In the illustrated embodiment, the internal coupling member 6 is in the form of a tubular permanent magnet. In other embodiments, the internal coupling member 6 can include an electromagnet or a non-permanent magnetic material. Moreover, all or only portions of the internal coupling member 6 can be magnetic. For example, a sidewall of the internal coupling member can be formed from or can include a magnet thereon to facilitate selective positioning of the internal coupling member by the external coupling member. A person skilled in the art will appreciate that various configurations are conceivable.

The magnetic scope manipulating system 2 can also include a tether for attachment to the internal coupling member. In the embodiment shown, a tether 24 is affixed at its distal end to the internal coupling member 6. The tether 24 can be any type of cable, wire or suture. Preferably, the tether 24 is flexible, non-magnetically-attractive and non-bioactive. In one embodiment, the tether 24 can be formed of a stainless steel or nylon mesh and/or can be coated with a smooth, low-friction outer jacket and/or lubricant to facilitate sliding within the working channels of a scoping device and within the anatomy of the subject.

While the tether 24 can have a variety of lengths, it is generally preferred that the length be greater than the length of the working channel 18 of the scoping device. In certain embodiments, the length of the tether 24 can be several meters longer than the length of the working channel 18 to provide enough slack for the surgeon to grasp the proximal end of the tether 24 while manipulating the distal end of the tether 24 within the subject.

The tether 24 can be attached to the internal coupling member 6 using a wide variety of methods known in the art, for example using glue, one or more screws or rivets, and/or welding. In the illustrated embodiment, the tether 24 is attached to an internal cylindrical surface 3 of the internal coupling member 6 using a rivet 5.

In use, the internal coupling member is configured to removably mate to the distal end of the scoping device, preferably with the tether extending through a working channel of the scoping device. While various mating techniques can be used, in an exemplary embodiment the internal coupling member 6 can be held against the distal end 12 of the scoping device 4 by applying tension to the tether 24. In such embodiments, the tether 24 can be fed through the scoping device 4 via one of the working channels 18. The diameter of the tether 24 can be made small enough to permit other surgical tools to be passed through the same working channel 18 through which the tether 24 is passed. The proximal end of the tether 24 can be left free, hanging out the proximal end of the scoping device 4 such that tension can readily be applied thereto by a user.

Figure 1B:
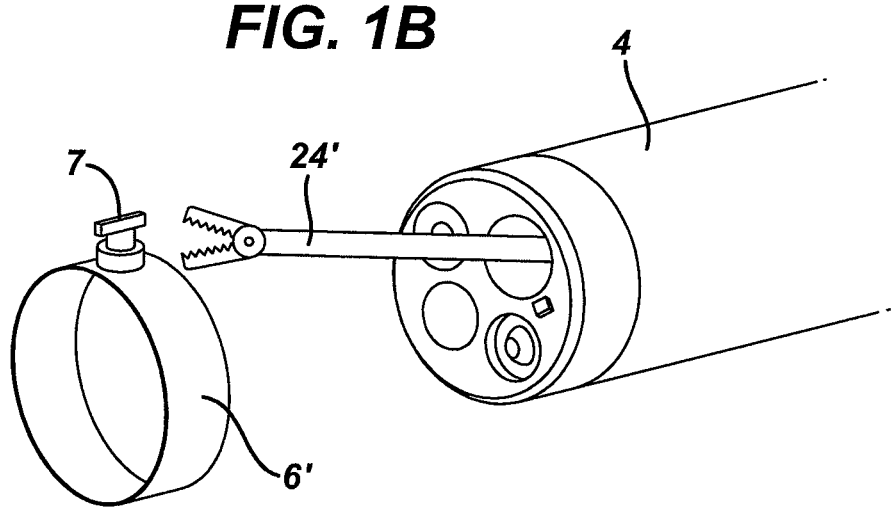
FIG. 1B is a perspective view of an internal coupling member having a feature formed thereon to facilitate grasping.

In another embodiment, the internal coupling member can be permanently or selectively attached to the distal end of the scoping device using an interference fit, threaded engagement, or other methods known in the art. The internal coupling member can also be disposed partially or completely around the scoping device and/or can be formed integrally with the scoping device. In certain embodiments, such as the embodiment shown in FIG. 1B, the internal coupling member 6' can be independent of the tether 24' and the tether 24' can be configured to grasp and/or release the internal coupling member 6'. The internal coupling member 6' can optionally include a feature 7 formed thereon to facilitate grasping by an endoscopic grasper or an endoscopic snare.

FIGS. 2A-2D illustrate one exemplary use of the magnetic scope manipulating system of FIG. 1A. Use of the system for performing a transrectal or transvaginal endoscopic procedure in a subject's abdominal cavity is illustrated. In such procedures, it can be desirable and/or necessary to advance the distal end of the scoping device from its point of entry in an inferior region of the cavity to a specific anatomical location in a superior region of the cavity.

Figure 2A:
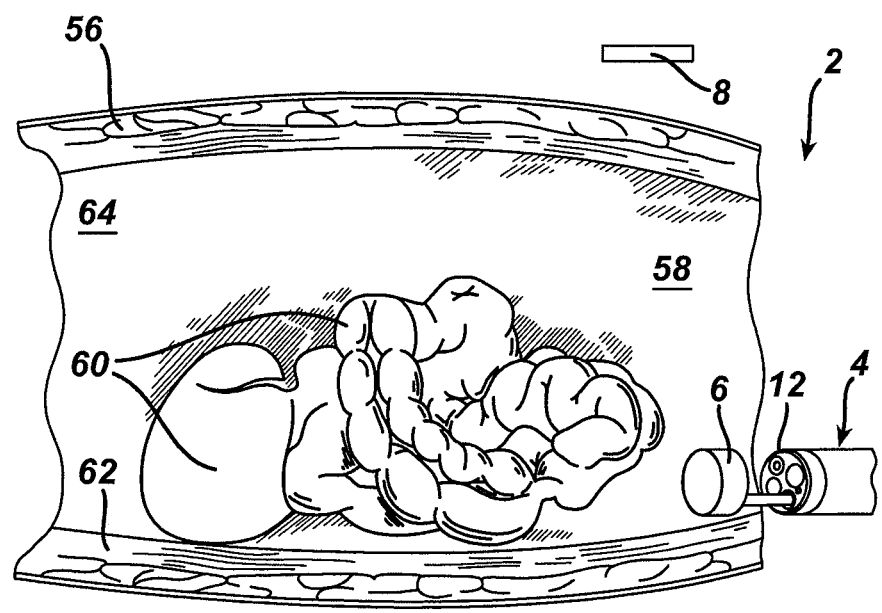
FIG. 2A is a partial cross-sectional view of a subject's abdominal cavity with a scoping device and an internal coupling member inserted therein.

FIG. 2A illustrates a cross-sectional view of a portion of a patient's abdomen. A layer of tissue forms a ventral wall 56 of the abdominal cavity 58. The viscera 60 contained within the abdominal cavity 58 are shown lying on the cavity's dorsal wall 62. This positioning of the viscera 60 is typical when the patient is placed in the supine position. The ventral wall 56 is separated from and elevated above the viscera 60 by insufflation gas introduced into the abdominal cavity 58 using methods known in the art. After accessing the abdominal cavity 58 using methods known in the art, the scoping device 4 is introduced into the cavity. As shown, gravity will tend to cause the scoping device 4 to lay on the dorsal wall 62 of the abdominal cavity 58 when the patient is in the supine position. Once a portion of the scoping device 4 is inserted into the abdominal cavity 58, it can be desirable to advance the distal end 12 of the scoping device 4 to a specific anatomical location 64 in order to carry out a procedure or to inspect the anatomical location 64.

Figure 2B:
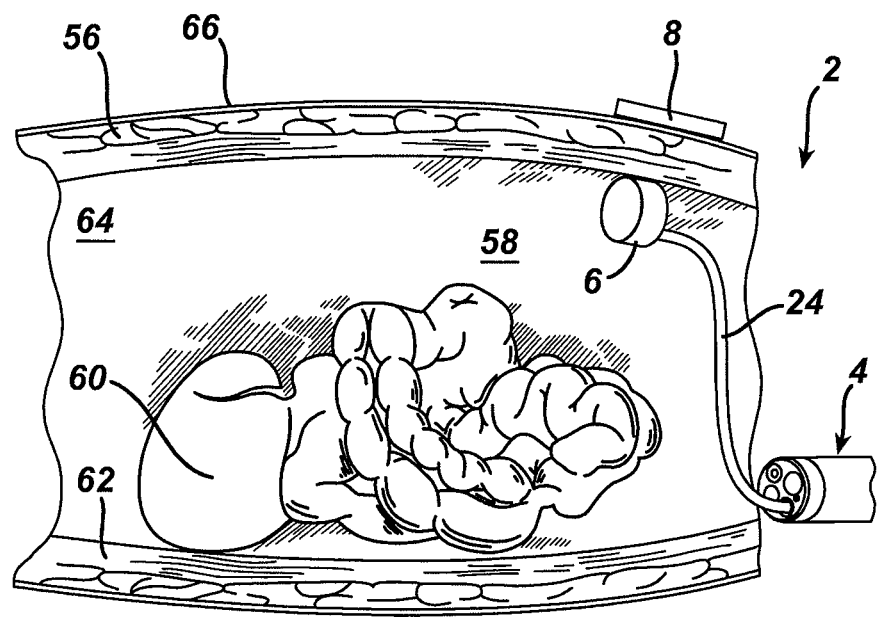
FIG. 2B is a partial cross-sectional view of the abdominal cavity of FIG. 2A with the internal coupling member drawn against a wall of the abdominal cavity by an external coupling member, and a tether extending from the internal coupling member through a channel in the scoping device.
Figure 2C:
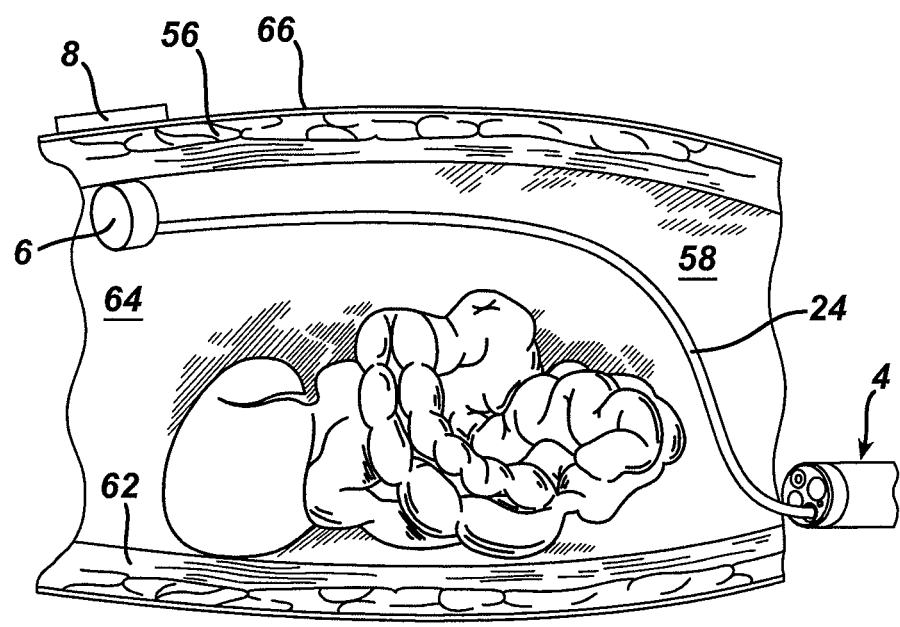
FIG. 2C is a partial cross-sectional view of the abdominal cavity of FIG. 2B with the internal coupling member drawn superiorly along a wall of the abdominal cavity by the external coupling member.
Figure 2D:
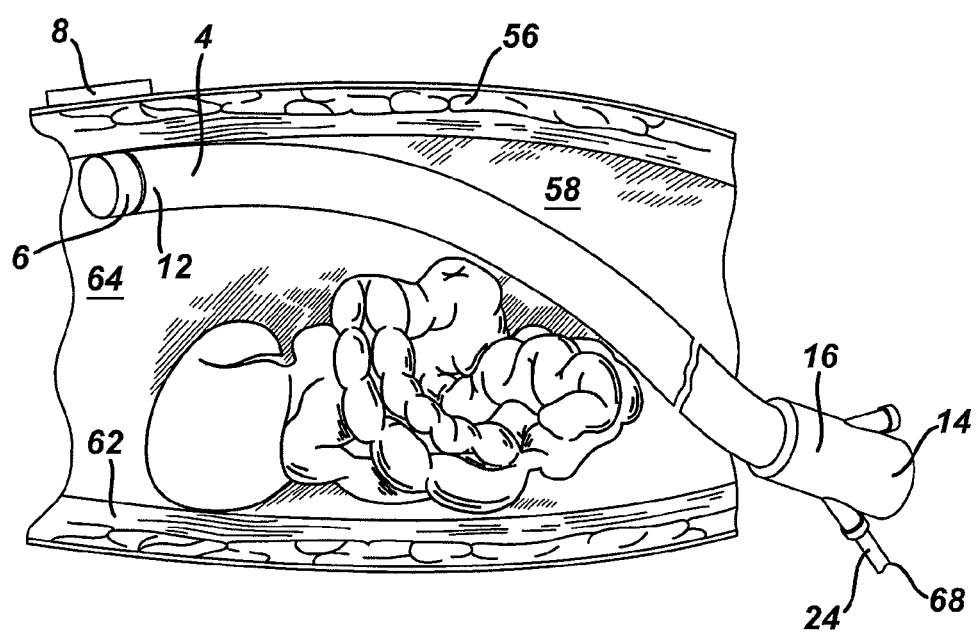
FIG. 2D is a partial cross-sectional view of the abdominal cavity of FIG. 2C with the scoping device advanced toward the internal coupling member along the tether.

This can be accomplished using the magnetic scope manipulating system 2 as shown in FIGS. 2B-2D. In one embodiment, the external coupling member 8 is placed outside of the subject, adjacent to the skin 66 that forms the exterior of the ventral wall 56 of the subject's abdominal cavity 58. The external coupling member 8, like the internal coupling member 6, can include one or more permanent magnets, one or more non-permanent magnets, one or more electromagnets, or any combination thereof. In a preferred embodiment, at least one of the internal coupling member or the external coupling member is either a permanent magnet or an electromagnet. Exemplary magnets include ceramic magnets, alnico magnets, composite-resin magnets, rare earth magnets such as samarium-cobalt magnets or neodymium-iron-boron magnets, iron-silicon alloy magnets, amorphous and/or nano-crystalline alloy magnets, nickel-iron alloy magnets, soft ferrite magnets, or any combination thereof. The magnetic strengths of the internal and external coupling members should be chosen such that they can attract or repel each other through the subject's ventral wall 56. In subjects with thicker abdominal walls 56, 62, stronger coupling members 6, 8 can be used. Since the external coupling member is positioned outside of the body, its size, mass, and composition is not as limited as that of the internal coupling member. As such, where a stronger coupling is required, the strength of the external coupling member is typically increased.

With the external coupling member 8 placed on or proximate to the skin 66 of the patient, the internal coupling member 6 can be magnetically attracted or coupled thereto. Tension on the tether 24 can be selectively released by the surgeon from the proximal end of the tether 24 to selectively permit the internal coupling member to move with respect to the scoping device 4. If the internal coupling member 6 does not immediately rise to the ventral wall 56 of the abdominal cavity 58 and remain magnetically suspended above the viscera 60 when the external coupling member 8 is introduced, the skin 66 and/or abdominal walls 62, 56 can be palpated, for example by manually pressing the abdominal walls 62, 56 inward against the insufflation fluid, to position the coupling members 6, 8 close enough to one another to facilitate magnetic coupling therebetween. In the illustrated embodiment, when the internal coupling member 6 is magnetically raised towards the external coupling member 8, a commensurate length of the tether 24 is drawn out of the working channel 18 of the scoping device 4. The scoping device, as a result of gravity, remains flat against the dorsal wall 62.

Once the internal and external coupling members 6, 8 are magnetically coupled through tissue, the external coupling member 8 can be moved as desired by the surgeon in order to effect a similar movement of the internal coupling member 6 and the tether 24 attached thereto. As shown in FIG. 2C, the external coupling member 8 can be moved superiorly along the patient's skin 66 to draw the internal coupling member 6 and the tether 24 attached thereto into the vicinity of the target anatomical location 64. As shown in FIG. 2D, by holding the proximal end 68 of the tether 24 to apply tension to the tether 24, the surgeon can advance the scoping device 4 along the tether 24, using the tether 24 in effect as a guide wire, until the distal end 12 of the scoping device 4 reaches the internal coupling member 6 in the vicinity of the target anatomical location 64.

The path taken by the scoping device 4 in the embodiment discussed herein with respect to FIGS. 2A-2D, up and over the viscera 60 through the void created by the insufflation gas, is a much cleaner, easier approach than if the scope were to be advanced using traditional methods of trying to force the scope through the viscera 60, along the dorsal wall 62. The position of the scoping device 4 against the ventral wall 56 also allows for better visualization of the target anatomical location 64, as the scoping device can now provide the surgeon with a view from above.

In other embodiments, where the internal coupling member 6 is formed integrally with the scoping device 4 or is rigidly attached thereto, the entire scoping device 4 can be drawn through the abdominal cavity 58 by manipulating the external coupling member 8. In such embodiments, the internal coupling member 6 can be either permanently or selectively attached to the scoping device.

Figure 3A:
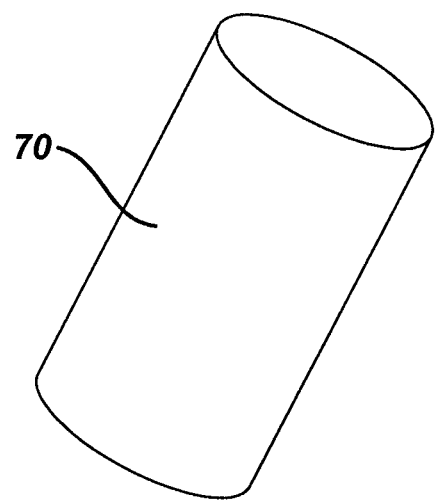
FIG. 3A is a perspective view of one embodiment of a tubular collar.
Figure 3B:
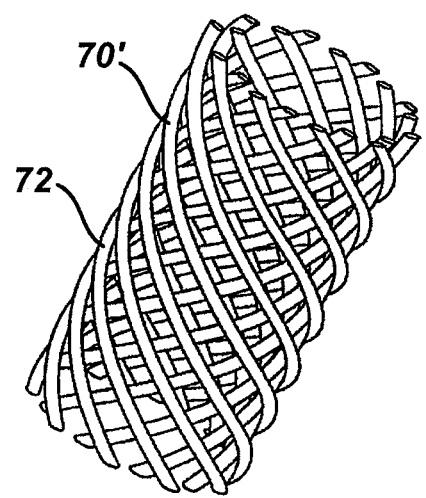
FIG. 3B is a perspective view of another embodiment of a tubular collar.

In other embodiments, the scoping device 4 can include a collar disposed therearound. The collar can be permanently attached to or integrally formed on the scoping device 4, or it can be slidable and/or removable. For example, in one embodiment a removable collar can be slid onto and off of the scoping device 4. In another embodiment, the removable collar can be formed of two interlocking halves of a cylinder. In this embodiment, the two interlocking halves can be selectively snapped together around the scoping device 4 or taken apart. FIGS. 3A and 3B show two exemplary collars. As shown in FIG. 3A, the collar 70 has a generally cylindrical shape and can be formed of a solid material. In the embodiment shown in FIG. 3B, the collar 70' is formed of a mesh material made up of several interwoven strands 72. The collar 70, 70' can include one or more permanent magnets, one or more non-permanent magnets, one or more electromagnets, or any combination thereof. The collar 70 or 70' can be positioned far enough from the distal end of the scoping device 4 that it will not magnetically couple to an internal coupling member positioned immediately adjacent thereto, unless desired. In one embodiment, the collar can be placed 100 mm from the distal tip of the scoping device 4.

Figure 4A:
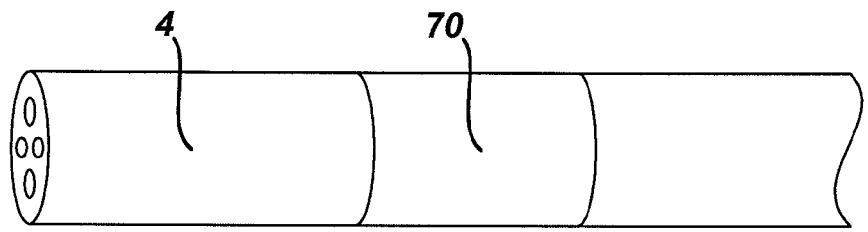
FIG. 4A is a perspective view of a scoping device having the tubular collar of FIG. 3A disposed thereon and within a recess.
Figure 4B:
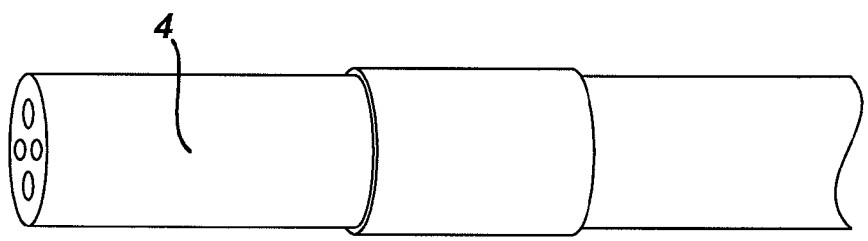
FIG. 4B is a perspective view of a scoping device having the tubular collar of FIG. 3A disposed thereon.
Figure 4C:
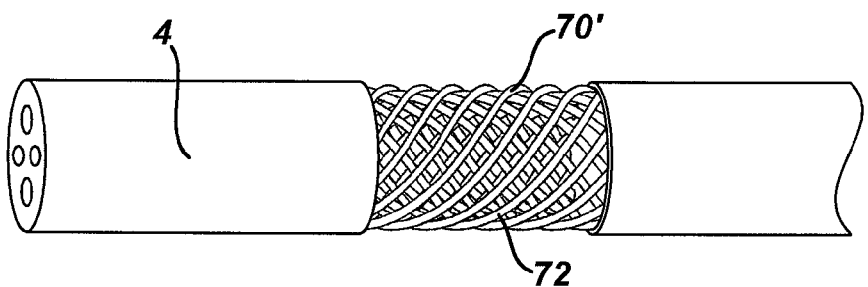
FIG. 4C is a perspective view of a scoping device having the tubular collar of FIG. 3B disposed thereon.
Figure 4D:
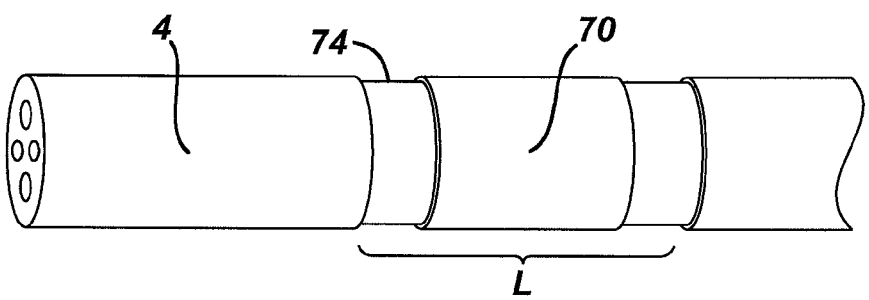
FIG. 4D is a perspective view of a scoping device having the tubular collar of FIG. 3A disposed within a channel formed in the exterior of the scoping device.

As shown in FIG. 4A, the collar 70 can be disposed around the scoping device 4. In the illustrated embodiment, a channel or recess 74 is formed about the circumference of the scoping device 4 having a depth approximately equivalent to the thickness of the walls of the collar 70 and a length approximately equivalent to the length of the collar 70. In such embodiments, the outer wall of the collar 70 sits flush with the outer wall of the scoping device 4, resulting in a constant diameter and continuous smooth surface. In other embodiments, as shown for example in FIG. 4B, the scoping device 4 can have no such channel 74, in which case the collar 70 will protrude slightly above the surface of the scoping device 4. FIG. 4C shows an embodiment similar to that shown in FIG. 4A, in which a mesh collar 70' is used. FIG. 4D illustrates another embodiment, in which the length L of the channel 74 formed about the circumference of the scoping device 4 exceeds that of the collar 70. In such embodiments, the collar 70 can be configured to slide longitudinally within the channel 74, along the outer surface of the scoping device 4.

In certain embodiments, the collar 70, 70' can be coupled to the scoping device 4 using any of a variety of methods known in the art. For example, the collar can be glued, welded, stapled, screwed, riveted, clipped, or molded to the scoping device 4. Where a flexible collar is used, the collar can optionally be sized with a slightly smaller diameter and have elastic properties that cause it to frictionally engage the scoping device 4.

Figure 5A:
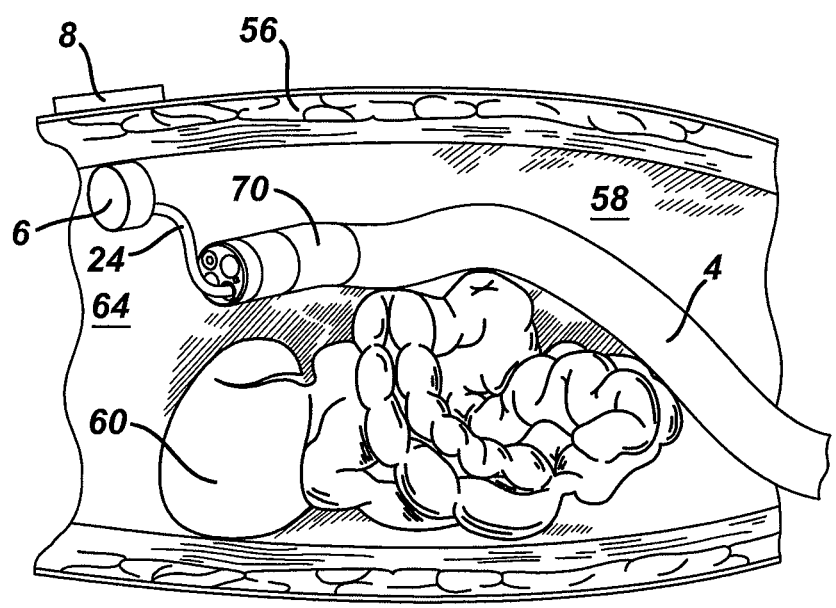
FIG. 5A is a partial cross-sectional view of a subject's abdominal cavity with a scoping device advanced distally into the subject, along a tether attached to an internal coupling member held against a wall of the abdominal cavity by an external coupling member.
Figure 5B:
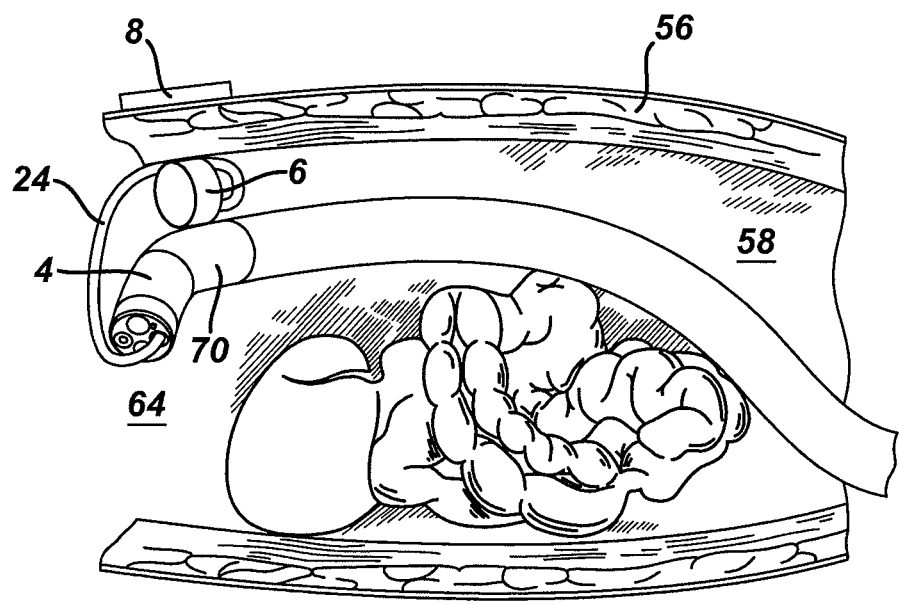
FIG. 5B is a partial cross-sectional view of the abdominal cavity of FIG. 5A with a collar disposed around the scoping device magnetically coupled to the internal coupling member.

FIGS. 5A and 5B illustrate an exemplary method of manipulating a scoping device having a collar 70 disposed therearound. First, an internal coupling member 6 attached to a tether 24 is advanced to a desired location within a subject's abdominal cavity as described herein with respect to FIGS. 2A-2C. The tether 24 can be front-loaded into a scoping device 4, meaning prior to inserting the scoping device into the patient, the tether is fed into the distal end of the working channel 18 until it passes out the proximal end. Tension can be applied to the tether 24 and, using the tether 24 as a guide wire, the scoping device 4 can be advanced distally into the subject as described herein with respect to FIG. 2D.

As shown in FIG. 5A, tension on the tether 24 can be released, allowing the scoping device 4 to lie on the viscera 60 within the abdominal cavity 58 and allowing gravity to pull the distal end of the scoping device 4 down and away from the internal coupling member 6, causing a portion of the tether 24 to be drawn out of the working channel 18 of the scoping device 4. With the distal end of the scoping device 4 dangling just below the internal coupling member 6, and the tension on the tether 24 released, the scoping device can be further advanced distally into the patient or otherwise manipulated by the surgeon until a collar 70 disposed therearound is magnetically coupled to the internal coupling member 6.

FIG. 5B illustrates the collar 70 of the scoping device 4 magnetically coupled to the internal coupling member 6, which is held against the ventral wall 56 of the patient's abdominal cavity 58 by magnetic attraction to the external coupling member 8. The scoping device 4 can now be articulated by the surgeon to provide a "bird's eye" view of the abdominal cavity. A grasping tool can be passed through a working channel 18 of the scoping device and can be used to pull the tether 24 completely out of the distal end of the working channel 18. The entire tether 24, including its free proximal end, can then be temporarily left within the patient and the grasping tool can be withdrawn proximally from the scoping device 4. Removing the tether 24 from the working channel 18 once the scoping device 4 is positioned as desired can be advantageous because it will free up additional room within the working channel 18 for carrying out surgical procedures. The grasping tool can either be passed through the same working channel as the tether 24 or can be passed through a different working channel.

Figure 6A:
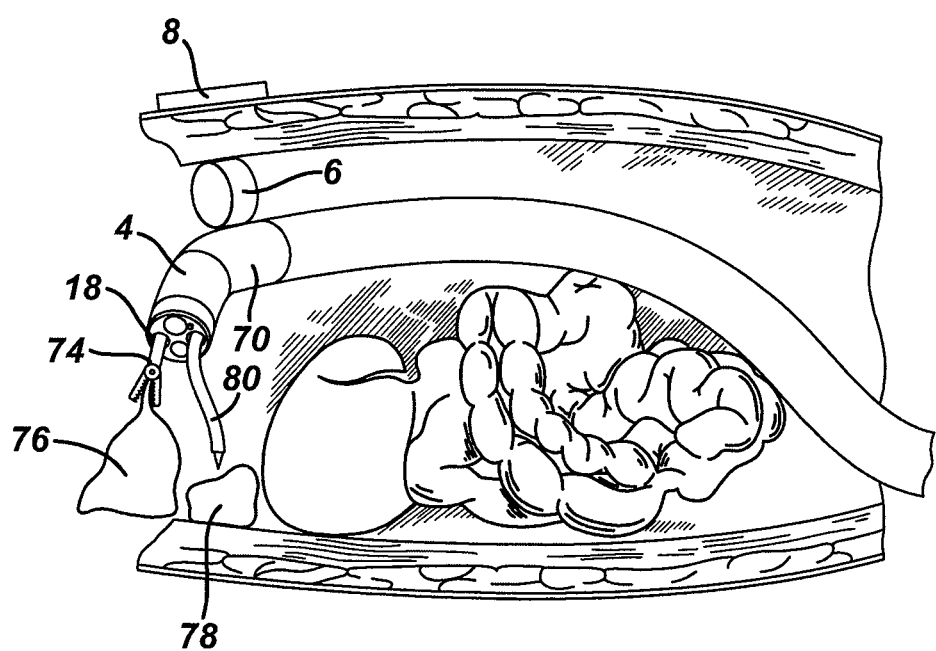
FIG. 6A is a partial cross-sectional view of a subject's abdominal cavity with a magnetic scope manipulating system positioned to hold a first organ out of the way while a procedure is conducted on a second organ.
Figure 6B:
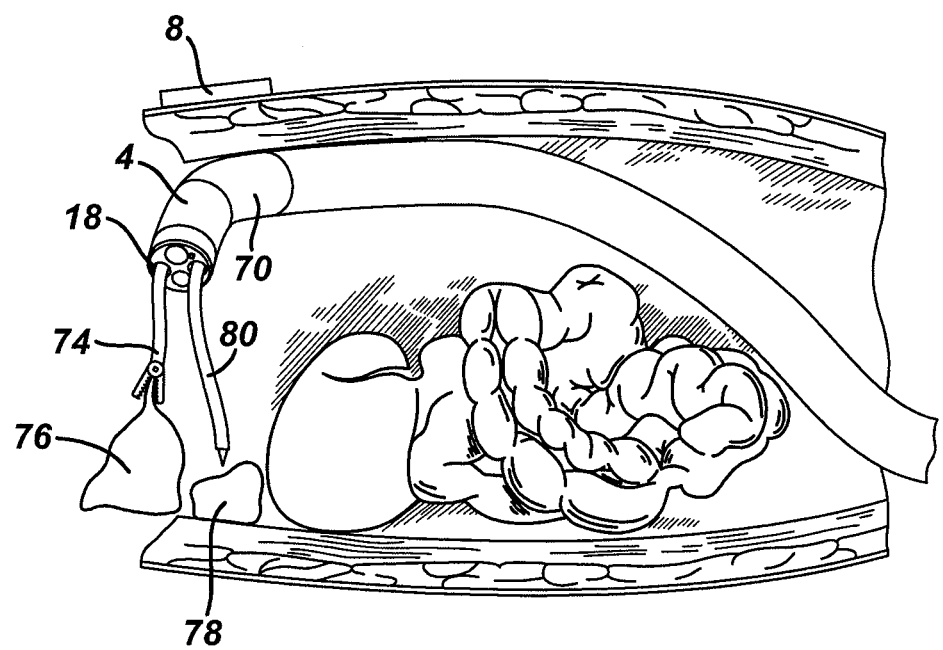
FIG. 6B is a partial cross-sectional view of a subject's abdominal cavity with a magnetic scope manipulating system positioned to hold a first organ out of the way while a procedure is conducted on a second organ, wherein a tubular collar is held against a wall of the abdominal cavity by an external coupling member.

With the scoping device 4 positioned as shown in FIG. 5B, it can be used to provide a leverage point for various surgical tools that can be passed through a working channel 18 of the scoping device 4. FIG. 6A illustrates one embodiment of a method of providing a leverage point within a patient. A surgical grasping tool 74 can be passed through a working channel 18 of the scoping device 4 and can be used to grasp an organ 76. As shown, if tension is then applied by the surgeon to the proximal end of the grasping tool 74, as if to draw the tool proximally out of the working channel 18, the organ 76 can be lifted against gravity, using the scoping device 4 as a leverage point. Once the organ 76 is lifted out of the way, the surgeon can access organs or other tissue 78 that were once covered by the organ 76 using a second surgical tool 80, passed through a second working channel 18 in the scoping device 4. In other embodiments, the grasping tool 74 and the second surgical tool 80 can be passed through the same working channel. FIG. 6B shows an alternate position of the scoping device 4, wherein the collar 70 is held directly against a wall of the abdominal cavity by the external coupling member 8, without the internal coupling member 6 positioned in between.

The method for providing a leverage point disclosed herein can be used in almost any portion of the abdominal cavity and further in almost any portion of the subject. For example, the scoping device 4 can be held against the dorsal wall or against a side wall of the subject's abdominal cavity, instead of the ventral wall as shown.

When the surgeon is ready to remove the scoping device 4 and/or the internal coupling member 6, graspers passed through a working channel 18 of the scoping device 4 can be used to feed the free proximal end of the tether 24 (the end opposite the internal coupling member) back into the distal end of the working channel until the free proximal end of the tether 24 passes out the proximal end of the working channel 18. The scoping device 4 can then be withdrawn proximally from the patient to disengage the collar 70 from the internal coupling member 6. Tension can then be applied to the tether 24 in order to pull the internal coupling member 6 attached thereto against the distal end of the scoping device 4. With tension maintained on the tether 24, the surgeon can then remove the entire system by withdrawing the scope proximally from the patient. The external coupling member 8 can be used to assist in withdrawing the system from the patient, or it can be turned off or moved a sufficient distance from the patient such that it no longer magnetically couples with the internal coupling member 6.

Figure 7:
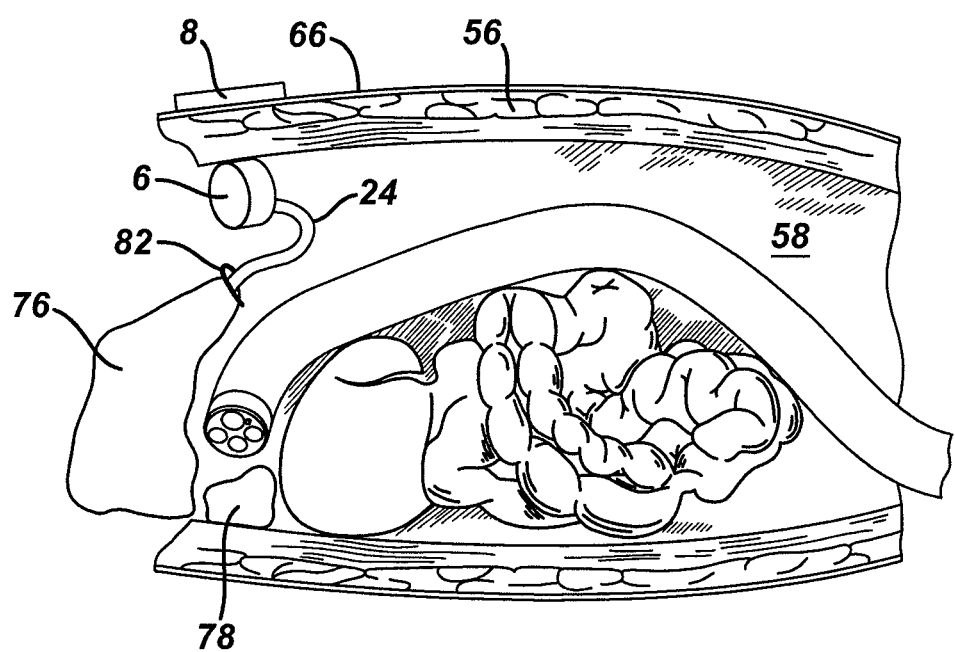
FIG. 7 is a partial cross-sectional view of a subject's abdominal cavity with a first organ tethered to an internal coupling member and held out of the way while a procedure is conducted on a second organ.

FIG. 7 illustrates a method of altering a position of an anatomical structure (e.g., an organ or other tissue within a patient). As shown, a scoping device 4 can be advanced into a subject's abdominal cavity 58 in accordance with the methods described herein. An internal coupling member 6 is shown held against the ventral wall 56 of the patient's abdominal cavity 58 via magnetic coupling to an external coupling member 8, placed against the subject's skin 66. In the illustrated embodiment, the tether 24 has been pulled distally out of the working channel 18 of the scoping device 4 using a grasper or other surgical tool as known in the art and described herein. Once removed from the working channel 18, the free end or some intermediate portion of the tether 24 can be attached to an organ 76 using a suture anchor 82 or other device or method known in the art. The organ 76 can be lifted using a grasper or other surgical tool prior to attachment to the tether 24, such that, once attached, the organ 76 is held above the other organs 78 and/or tissue positioned beneath it. As shown, the organ 76 is attached to the tether 24 using a suture anchor 82. As described above, the tether 24 is also attached to the internal coupling member 6, which is magnetically coupled to the external coupling member 8 through the patient's skin 66 and ventral abdominal wall 56. The external coupling member 8 can be repositioned as desired by the surgeon in order to magnetically effect movement of the internal coupling member 6 and the organ 76 coupled thereto via the tether 24. In this manner, the surgeon can move or otherwise manipulate the organ 76 as needed to access tissue or other organs 78 lying beneath.

When desired, a grasper or other surgical tool can be passed through the working channel 18 of the scoping device 4 and can be used to release the suture anchor 82 from the organ 76 and/or the tether 24. The suture anchor 82 can then be removed from the patient via the grasper and the working channel 18. The grasper can then be re-inserted via the working channel 18 and can be used to feed the free end of the tether 24 into the distal end of a working channel 18, until the free end passes out the proximal end of the scoping device 4, where it can be grasped by the surgeon. The tether 24, the internal coupling member 6, and the scoping device 4 can then be removed from the patient as described herein.

While use of the magnetic scope manipulating device 2 within the abdominal cavity is discussed at length herein, the system can be used in almost any portion of a patient, and its use is not by any means limited to within the abdominal cavity. Additionally, a person skilled in the art will appreciate that, while the methods and devices are described in connection with minimally invasive procedures, such as endoscopic procedures, the methods and devices disclosed herein can be used in numerous surgical procedures. By way of non-limiting example, the devices can be used in laparoscopic procedures, in which the device is introduced percutaneously, and more preferably through an introducer, such as a cannula or trocar. The methods and devices can also be used in arthroscopic and/or open surgical procedures.

Further, the methods and devices disclosed herein can be applied in fields beyond the medical industry. In fact, any application where a scoping device is used in an area with limited accessibility can benefit from such methods and devices. In the plumbing industry for example, scoping devices can be used to view the interior of a drain or other pipe to locate blockages or deterioration. Similarly, in the course of repairing or inspecting engines or other complex machines, a scoping device can be used to provide visibility into the interior of the machine without completely disassembling it. It is understood that in procedures like these, the methods and devices disclosed herein can be readily applied.

The devices and methods described herein can also be used in other applications where a flexible, elongate object must be guided through a path laden with obstacles. In the construction field for example, the devices and methods described herein can be used to run electrical or other wires through a finished wall or ceiling.

The devices disclosed herein can be designed to be disposed of after a single use, or can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used tool is obtained and if necessary cleaned. The tool can then be sterilized. In one sterilization technique, the tool is placed in a closed and sealed container, such as a plastic or TYVEK bag. The container and tool are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. It is preferred that the device is sterilized. This can be done by any number of ways known to those skilled in the art including beta or gamma radiation, ethylene oxide, or steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A system for manipulating a scoping device, comprising:
    a scoping device having at least one working channel extending therethrough, the at least one working channel having a proximal end and a distal end;
    a tether extending through the at least one working channel of the scoping device; and
    an internal coupling member attached to a distal end of the tether and positionable adjacent to a distal end of the scoping device, the internal coupling member configured to be magnetically coupled to an external coupling member and having a working channel extending from a proximal end of the internal coupling member to a distal end of the internal coupling member,
    wherein, when the internal coupling member positioned adjacent to the distal end of the scoping device, a longitudinal axis of the working channel of the internal coupling member is parallel to a longitudinal axis of the at least one working channel of the scoping device such that a tool can be inserted into the proximal end of the at least one working channel of the scoping device and advanced to extend out of a distal end of the working channel of the internal coupling member; and
    wherein the scoping device includes at least one magnetically-attracted collar disposed therearound and positioned proximal to the distal end of the scoping device.

2. The system of claim 1, wherein the internal coupling member comprises a magnet.

3. The system of claim 1, wherein the scoping device is an endoscope.

4. The system of claim 1, wherein the internal coupling member has a generally tubular shape.

5. The system of claim 1, wherein the internal coupling member includes a feature formed thereon configured to be grasped by a surgical tool.

6. The system of claim 1, wherein the internal coupling member is removably attached to the distal end of the scoping device.

7. The system of claim 1, wherein the internal coupling member includes at least one magnet selected from the group consisting of an electromagnet, a permanent magnet, and a non-permanent magnet.

8. The system of claim 1, further comprising an external coupling member.

9. The system of claim 8, wherein the external coupling member includes at least one magnet selected from the group consisting of an electromagnet, a permanent magnet, and a non-permanent magnet.

10. The system of claim 1, wherein the at least one collar is slidably disposed around the scoping device.

11. The system of claim 1, wherein the at least one collar is formed of a flexible mesh.

12. The system of claim 1, wherein the collar includes at least one magnet selected from the group consisting of an electromagnet, a permanent magnet, and a non-permanent magnet.

* * * * *